United States Patent [19]
Lamartine et al.

[11] Patent Number: 5,952,526
[45] Date of Patent: *Sep. 14, 1999

[54] PROCESS FOR THE DEALKYLATING SULFONATION OF P-ALKYL CALIXARENES

[75] Inventors: Roger Lamartine, Villeurbanne; Jean-Bernard Regnouf de Vains, Lyons, both of France; Philippe Choquard, Cologny/Genève, Switzerland; Arnold Marcillac, Sorlin en Bugey, France

[73] Assignee: Transdiffusia S.A., Geneva, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/671,170

[22] Filed: Jun. 26, 1996

[51] Int. Cl.⁶ .................................................. C07C 309/32
[52] U.S. Cl. ................................................ 562/74; 562/82
[58] Field of Search ................................... 562/88, 82, 74

[56] References Cited

FOREIGN PATENT DOCUMENTS 9212708  8/1992  WIPO .

OTHER PUBLICATIONS

March, Advanced Organic Chemistry pp. 528–529, 561–563, 1992.
Chawla, et al., Synth. React. Inorg. Met.–Org. Chem., 26(5), 775–790, May 1996.
J. Chem. Soc. Perkin Transactions I (Shinkai, et al.).
J. Am. Chem. Soc. 117, No. 46 (Steed, et al.).
J. Chem. Soc. Perkin Transactions II (Lambrechts, et al.).
New J. Chem. 15 (1991), 8883–7.

*Primary Examiner*—Robert Gerstl
*Attorney, Agent, or Firm*—Robin, Blecker & Daley

[57] ABSTRACT

Para sulfonated calixarenes are obtained in a one-step reaction directly from para blocked calixarenes by treating same with a sulfonating agent, such as concentrated sulfuric acid, to perform an ipso-electrophilic substitution.

8 Claims, No Drawings

PROCESS FOR THE DEALKYLATING SULFONATION OF P-ALKYL CALIXARENES

BACKGROUND OF THE INVENTION

1. Field of the Invention

The present invention refers to a new and useful process for the preparation of para sulfonated calixarenes. In particular, the invention relates to a process for the preparation of calixarene p-sulfonic acids starting from calixarenes which are para substituted by a blocking group, e.g. p-alkyl calixarenes.

Calixarenes are macrocyclic phenolic compounds that are generally prepared from phenolic compounds by condensation in an acid or basic environment with an aldehyde such as formaldehyde, an alkylaldehyde, an arylaldehyde, or a heteroarylaldehyde, preferably formaldehyde. These macrocycles which are shortly named "calixarenes" are of the type of tetra-p-tert-butyl-calix[4]arenes or pentacyclo-[19.3.1.$^{13,7}$.1$^{9,13}$.1$^{15,19}$] octacosa-1(25),3,5,7(28),9,11,13 (27),15,17,19(26),21,23-dodecaene and their analogous compounds, namely the [5], [6], [7], [8], [9] and [10] arene analogues.

The utility of the calixarenes is based on their capability of forming complexes, adducts and/or inclusion compounds with neutral or ionic organic and inorganic compounds; furthermore, calixarenes are outstandingly stable and resistant to high temperatures and chemical attacks in aggressive environments.

A serious problem which is encountered in the industrial application of these macrocycles stems from their insolubility in protic solvents such as water and the alcohols. One possibility of overcoming this problem and to make them soluble is to introduce solubilizing groups, preferably sulfonic acid groups, in the para position to the hydroxy groups in the phenolic nuclei, giving sulfonated calixarenes. Such water soluble calixarene derivatives have proven to be useful in a great number of fields, especially in pharmacology, and still more application fields are currently opened, such as catalysts or catalyst intermediates.

2. Description of the Prior Art

Sulfonation of calixarenes that are unsubstituted in the para position of the phenolic OH group has already become known, see, e.g., Japanese patent No. 61-083156 to Sugai Chemical Industry Co. Ltd. However, calixarenes must be prepared from para substituted phenols where this para substituent is a blocking group to render the para position inaccessible; otherwise, a free para position of the phenol does not yield appreciable amounts of calixarenes during reaction with aldehydes but rather the well known phenolic resins. Therefore, it is necessary in the synthesis of calixarenes to start from para substituted phenols. Of course, such starting phenols are preferred where the para blocking substituent is rather easily removable; such substituents are, e.g., alkyl groups such as the tert-butyl group.

Until now, sulfonation of para alkyl substituted calixarenes has been effected by a multistep process. First, the para alkylated calixarene is prepared which is then dealkylated by an reversed Friedel-Crafts reaction to yield the para unsubstituted calixarenes. In a further step, the calixarene is reacted with hot concentrated sulfuric acid.

SUMMARY OF THE INVENTION

A first and major objective of the present invention is to develop and to provide an improved process for the preparation of p-sulfonated calixarenes starting from p-alkylated calixarenes which avoids the drawbacks of the known multistage method; these drawbacks are mainly: low yield of the final product, necessity of using special reagents for dealkylation, of working in an anhydrous medium, of conducting an intermediate isolation and sometimes purification step, and waste of time.

Another object of the invention is to provide such a preparation process which gives high yields and which does not normally require a special purification of the sulfonated calixarenes to be obtained.

These objects are now met by the new process which comprises a one-step reaction of para substituted calixarenes with a sulfonating agent and the recovering of the calixarene sulfonic acids directly from the reaction mixture.

It has been highly surprising that the simultaneous dealkylation and sulfonation could be obtained, according to the invention, in one step and with a sulfonating agent only; the one skilled in the art would have expected an electrophilic substitution reaction of one or more of the free hydrogen atoms of the p-substituted calixarenes and never an ipso-electrophilic substitution on the para carbon atoms which carry the blocking substituent.

A preferred sulfonating agent is concentrated sulfuric acid. However, other known sulfonating agents may also be used.

The reaction is preferably carried out at a temperature that should not substantially exceed 80° C. in order to avoid secondary reactions. The time period of the reaction is about 2 to 4 hours. After this time, the reaction mixture is cooled down and filtered, in a manner which will be described below, in order to eliminate the excess of sulfonating agent and unreacted starting calixarene.

Preferably, the process is conducted in such a manner that, at the beginning of the reaction, the molar ratio of sulfuric acid to p-substituted calixarenes is essentially selected to the stoechiometric one in order to avoid losses of the valuable sulfonated product during processing after the sulfonation. It should however be noted that the sulfonating agent, i.e. concentrated sulfuric acid, does additionally act as a solvent for the rection products. Thus, an excess is to be added over the stoechiometric amount, and the minimum volume of sulfuric acid to be used will be different for each calixarene species. However, if the reaction time is increased, a substantially complete transformation into calixarene sulfonic acids can be achieved.

The process of the invention can thus be summarized by the following reaction scheme:

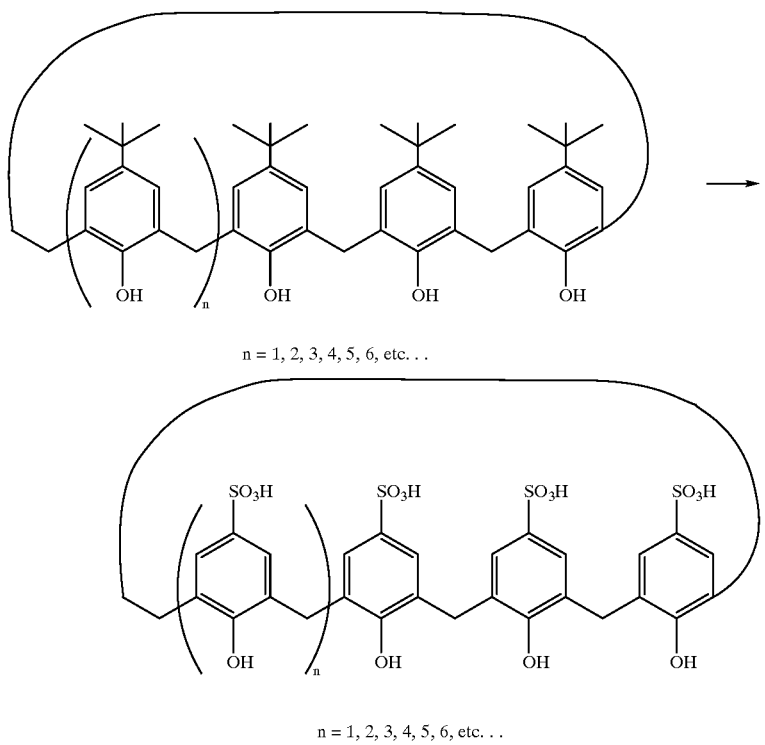

n = 1, 2, 3, 4, 5, 6, etc...

n = 1, 2, 3, 4, 5, 6, etc...

These and other objects and features of the invention will be better understood by reference to the detailed description which follows.

DETAILED DESCRIPTION OF THE INVENTION

As to the recovery of the sulfonated products already summarily described above, the reaction mixture, comprising sulfonating agent (typically sulfuric acid), sulfonated calixarene and unsulfonated, residual calixarene, is cooled down or allowed to cool to room temperature. The heterogeneous reaction mixture is then filtered and smoothly compressed on the filter in order to eliminate most of the excess sulfonating agent, i.e. sulfuric acid; the acidic filtrate is put aside. The solid residue, comprising sulfonated calixarene, unreacted, residual starting calixarene, and traces of sulfonating agent, is very rapid washed with a very small volume of cold ethanol in order to remove said traces of sulfonating agent. The corresponding filtrate is put aside. The washed filter residue is suspended at room temperature in methanol and filtered to obtain a second, purified residue that is constituted by unreacted calixarene.

The methanolic filtrate is concentrated, discolored by means of active charcoal and then poured into excess ethyl acetate under stirring. The cream white precipitate is filtered, the residue is dried during several hours in vacuo at 30 to 40° C. The analyses of the sulfonated calixarenes thus obtained are in conformity with literature values with the exception that they contain less water. The absence of free sulfuric acid is made by barium sulfate precipitation in a test solution of the sulfonated calixarenes to which a barium chloride solution is added.

The unreacted calixarene derivative may be recycled to another, new reaction batch.

The following Examples further illustrate the invention. These Examples are thus given for illustration purposes only and are not construed to limit the invention in any way.

EXAMPLE 1

Preparation of calix[4]arene-5,11,17,23-tetrasulfonic acid

In a flask equipped with a reflux condenser and a magnetic stirrer, 5 grams (7.7 mmoles) of tetra-p-tert-butyl-calix[4] arene are carefully added, portionwise and under stirring, to 20 ml of concentrated sulfuric acid (95 to 97%, Merck). The suspension which is formed is heated during 4 hours to about 80° C. The real duration of the reaction depends upon the result of a final water solubility test of a sample taken from the mixture from time to time.

When there is no precipitate detectable with the naked eye any more, the mixture is allowed to cool, and the precipitate is carefully filtered off on a fritted glass filter having the porosity of 3 or 4. The porosity of 3 is preferred since it requires a low suction force and a better flow of the viscous filtrate. The brown solid recovered on the filter is washed twice with 2.5 ml of ice cold ethanol, the washings being collected in another vessel. The residue which is now freed from excess sulfuric acid is treated until total solution with several fractions of methanol, and the final volume of this solution is about 100 ml.

The solution is now treated with 1 gram of decoloring charcoal, filtered on celite, and added to 500 ml of ethyl acetate under stirring. The precipitate which forms gradually acquires a structural form and is then filtered, and the residue is dried under high vacuum at 30 to 40° C., yielding 5 grams (6.7 mmoles, 87%) of calix[4]arene-5,11,17,23-tetrasulfonic acid as a clear brown powder.

Analysis: $^1$H-NMR: 5.08 (s, 4 Ar—$CH_2$—Ar); 5.97 (s, 14H, (8 acidic H exchanged+3 $H_2O$)); 8.66 (s, 8H of Ar). $^{13}$C-NMR: 35.02 (Ar—$CH_2$—Ar); 131.02 (C(H) of Ar); 132.53 (Ar—$CH_2$—Ar); 140.29 and 155.95 (C—OH and C—$SO_3$H). ES-MS, negative mode: 743 (M-H)$^-$; 371

$(M-2H)^{2-}$ /2; 247 $(M-3H)^{3-}$ /3; 185 $(M-4H)^{4-}$ /4; 393$(M-2H-2H+2Na)^{2-}$ /2; 382 $(M-2H-H+Na)^{2-}$ /2; 254 $(M-3H-H+Na)^{3-}$ /3.

EXAMPLE 2

Preparation of calix[8]arene-5,11,17,23,29,35,41,47-octasulfonic acid

Example 1 was repeated with the exception that 5 grams (3.85 mmoles) of octa-p-tert-butylcalix[8]arene were used instead of the corresponding calix[4]arene derivative. 2.75 grams of calix[8]arene-5,11,17,23,29,35,41,47-octasulfonic acid were finally obtained in a 48% yield.

Analysis: 1H-NMR: 4.40 (s, 8 Ar—$CH_2$—Ar); 5.26(s, 28 H, 16 exchanged acid H+6$H_2O$); 7.87 (s, 8 H of Ar). 13C-NMR: 33.91 (Ar—$CH_2$—Ar); 129.50 C(H) of Ar); 131.36 (Ar—$CH_2$—Ar); 138.49 and 156.63 (C—OH and C—$SO_3H$). ES-MS, negative mode: 743 $(M-2H)^{2-}$ /2; 495 $(M-3H)^{3-}$ /3; 371 $(M-4H)^{4-}$ /4.

The following compounds have been synthesized by the process of the present invention:

1) Calix[4]arene-5,11,17,23-tetrasulfonic acid,
2) calix[5]arene-5,11,17,23,29-pentasulfonic acid,
3) calix[6]arene-5,11,17,23,29,35-hexasulfonic acid,
4) calix[7]arene-5,11,17,23,29,35,41-heptasulfonic acid,
5) calix[8]arene-5,11,17,23,29,35,41,47-octasulfonic acid,
6) calix[9]arene-5,11,17,23,29,35,41,47,53-nonasulfonic acid,
7) calix[10]arene-5,11,17,23,29,35,41,47,53,59-decasulfonic acid.

The invention is not limited to the disclosure in the detailed description above. For example, reaction and post-treatment conditions may be changed and optimized without departing from the scope of the invention as defined in the appended claims.

We claim:

1. A process for the preparation of calixarene-p-sulfonic acids wherein a starting calixarene, substituted in the para positions of its aromatic rings by a blocking group, is reacted with concentrated sulfuric acid, the process comprising treating said starting calixarene at a temperature not substantially exceeding 80° C. with concentrated sulfuric acid in a stoichiometric amount of at most 6.1; removing excess sulfuric acid from the reaction mixture after cooling to room temperature; treating the residue with a cold alcohol; treating the washed residue with methanol and filtering; and recovering pure, free calixarene-p-sulfonic acid having a defined degree of hydration from the methanolic filtrate.

2. The process of claim 1, wherein said para blocking group is an alkyl group.

3. The process of claim 2, wherein said para blocking group is a tertiary butyl group.

4. The process of claim 1, wherein said alcohol is ethanol.

5. The process of claim 1, wherein the reaction is carried out at a temperature not higher than 80° C. for about 2 to 4 hours.

6. The process of claim 1, wherein the reaction mixture comprises an excess of at most 5.1 times the stoichiometrically necessary amount of sulfuric acid, acid insoluble unreacted starting compound and insoluble calixarene-p-sulfonic acid is filtered to remove said excess of sulfuric acid, and the calixarene-p-sulfonic acid is recovered from the filter residue by dissolution in methanol, filtration and precipitation by ethyl acetate.

7. Calix[4]arene-5,11,17,23-tetrasulfonic acid containing 3 molecules of hydration water, obtained by the process of claim 6.

8. Calix[8]arene-5,11,17,23,29,35,41,47 octasulfonic acid containing 6 molecules of hydration water, obtained by the process of claim 6.

* * * * *